(12) United States Patent
DeGraw

(10) Patent No.: US 11,247,999 B1
(45) Date of Patent: Feb. 15, 2022

(54) FACILE CONVERSION OF MORPHINE TO NORMORPHINE

(71) Applicant: Joseph DeGraw, Mountain Brook, AL (US)

(72) Inventor: Joseph DeGraw, Mountain Brook, AL (US)

(*) Notice: Subject to any disclaimer, the term of this patent is extended or adjusted under 35 U.S.C. 154(b) by 0 days.

(21) Appl. No.: 17/367,251

(22) Filed: Jul. 2, 2021

(51) Int. Cl.
 *C07D 489/09* (2006.01)

(52) U.S. Cl.
 CPC .................................. *C07D 489/09* (2013.01)

(58) Field of Classification Search
 CPC ...................................................... C07D 489/09
 See application file for complete search history.

(56) References Cited

U.S. PATENT DOCUMENTS

| 2,885,401 | A | | 5/1959 | Grüssner et al. |
| 2,890,221 | A | | 6/1959 | Rapoport |
| 2,891,954 | A | | 6/1959 | Weijlard |
| 3,230,224 | A | | 1/1966 | Sawa et al. |
| 3,254,088 | A | | 5/1966 | Juda et al. |
| 3,905,981 | A | * | 9/1975 | Olofson ............... C07D 489/08 546/44 |
| 5,112,975 | A | * | 5/1992 | Wallace ............... C07D 489/08 546/44 |
| 6,972,332 | B1 | | 12/2005 | Francis |
| 7,629,355 | B2 | | 12/2009 | Lawson |
| 9,073,934 | B2 | * | 7/2015 | Scammells .......... C07D 489/00 |
| 2011/0313163 | A1 | * | 12/2011 | Hudlicky ............. C07D 489/02 546/39 |
| 2016/0159812 | A1 | * | 6/2016 | Weber .................. C07D 489/08 546/45 |

FOREIGN PATENT DOCUMENTS

| AU | 2011276978 A1 | | 1/2012 |
| CN | 101570539 | * | 11/2009 |
| CN | 104507947 A | | 4/2015 |
| CN | 104470928 B | | 8/2017 |
| CN | 110330500 | * | 10/2019 |
| EP | 0158476 B1 | | 10/1985 |
| RU | 2007139827 A | | 5/2009 |

OTHER PUBLICATIONS

Borowitz; J. Heterocycl. Chem. 1975, 12, 1123-1126. doi: 10.1002/jhet.5570120607 (Year: 1975).*
Coop; J. Org. Chem. 1998, 63, 4392-4396. doi: 10.1021/JO9801972 (Year: 1998).*

(Continued)

*Primary Examiner* — Daniel R Carcanague
(74) *Attorney, Agent, or Firm* — Houda El-Jarrah; Bold IP, PLLC

(57) ABSTRACT

There are provided methods of making an N-demethylated derivative of morphine namely, normorphine. The normorphine can be substituted at the N—H position with various ligands that may result in new useful morphine derivatives. These derivatives may have increased analgesic efficacy, have less addictive properties, and/or have effective anti-opiate properties capable of rescuing overdosed persons or lead to recovery from conditions caused by opiate drug abuse.

14 Claims, 3 Drawing Sheets

| KEY | |
|---|---|
| I | $R_1 = CH_3$; $R_2 = H$ |
| II | $R_1 = \overset{O}{\overset{\|}{C}}-OCH_3$; $R_2 = \overset{O}{\overset{\|}{C}}-OCH_3$ |
| III | $R_1 = H$; $R_2 = H$ |

(56) References Cited

OTHER PUBLICATIONS

Hosztafi; Synth. Commun. 1992, 22, 1673-1682. doi: 10.1080/00397919208020486 (Year: 1992).*
Montzka; Tetrahedron Letters 1974, 1325-1327. doi: 10.1016/S0040-4039(01)82479-5 (Year: 1974).*
Oguri; Chem Pharm Bull 1989, 37, 955-957. doi: 10.1248/cpb.37.955 (Year: 1989).*
Portoghese; Journal of Medicinal Chemistry 1972, 15, 208-210. doi: 10.1021/jm00272a025 (Year: 1972).*
Rice; J. Med. Chem. 1975, 18, 10, 1033-1035. doi: 10.1021/jm00244a019 (Year: 1975).*
Rice; J. Heterocycl. Chem. 1977, 14, 665-666. doi: 10.1002/jhet.5570140424 (Year: 1977).*

* cited by examiner

| KEY | |
|---|---|
| I | $R_1 = CH_3$; $R_2 = H$ |
| II | $R_1 = \overset{O}{\overset{\|}{C}}-OCH_3$; $R_2 = \overset{O}{\overset{\|}{C}}-OCH_3$ |
| III | $R_1 = H$; $R_2 = H$ |

FACILE CONVERSION OF MORPHINE TO NORMORPHINE

FIELD OF THE INVENTION

The present technology relates to morphine-related chemicals that may be used in the production of chemicals useful in the treatment of medical conditions, including pain.

BACKGROUND

Morphine is one of the most well-known analgesics (pain killers) and its use is widespread. Though it is regarded as highly effective, morphine is known to be addictive. There has been ongoing research into developing non-addictive pain killers, as a potential substitute for morphine. One approach has been to create chemical variants of morphine by replacing the N-methyl group of the molecule with other functional groups that would produce a product that retains the pain killing efficacy of morphine but which is either non-addictive or less addictive. Other molecules of interest contain N-substituents that increase analgesic efficacy, such as fentanyl. Still others cause opiate antagonism and are used to reverse the effects of overdosing, such as the drug N-allyl morphine (nalorphine, formerly also known under the trademark, NALLINE).

In the meantime, other pain-killers have been developed. Some have shown promise but have ultimately had issues with regard to addiction of the patients. As a result, there is an ongoing need in the treatment of pain for a non-addictive pain killer that is less time consuming to produce, and hence less expensive.

SUMMARY

To the extent future research into morphine-based analgesics focus on variants at the N-substituent, this will require the ready availability of the N-demethylated morphine compound, namely, normorphine. According to an exemplary embodiment, there is provided a simpler, more efficient, process to produce this basic material for the development of morphine-based analgesics.

The reaction product includes a yield of normorphine. The normorphine can be separated from reaction byproducts and purified by conventional techniques.

The present technology provides an exemplary method of making normorphine (III) that includes several sequential process steps. These steps include but are not limited to:

preparing a solution of bis-carbonate of morphine in a solution;

combining the bis-carbonate solution with a reductive agent, such as L-selectride, in a solvent tetrahydrofuran as a mixture;

refluxing the mixture;

quenching any remaining reagent in the refluxed mixture;

evaporating the solvent to produce a residue;

homogenizing the residue with water;

acidifying the homogenized residue;

neutralizing the acidified homogenized residue;

separating and removing an aqueous layer from the neutralized homogenized residue;

cooling the aqueous layer and adjusting the pH to the range about 8 to about 9 to produce a crystalline precipitate; and filtering to collect a reaction product comprising normorphine (III).

While the reductive agent in an exemplary embodiment is L-selectride, of course other reductive agents may be used. The reductive agent is not limited to L-selectride.

The reaction product from the process described herein below produces normorphine at a high yield and purity. The process includes the treatment of morphine with a chloroformate, such as exemplified by methyl chloroformate, which results in displacement of the N—$CH_3$ group and functionalization of the N and the 3-OH groups of the molecule to yield a biscarbonate. The second of two steps in the process involves a reductive cleavage of both carbonate moieties, with a reductive agent.

The description here below enlarges upon this summary and provides additional details as well as an illustrative example of the methods according to the inventive technology.

BRIEF DESCRIPTION OF THE DRAWINGS

The attached Figures are not to scale and are merely intended to illustrate aspects of the technology described herein and claimed here below.

DETAILED DESCRIPTION

There are provided methods of making an N-demethylated derivative of morphine namely, normorphine. The normorphine can be subsequently substituted at the N—H position with various ligands (i.e. it may be functionalized) to produce new, useful morphine derivatives. These derivatives may have increased analgesic efficacy, have fewer addictive properties, and/or have effective anti-opiate drugs capable of rescuing overdosed persons, and/or lead to recovery from conditions caused by opiate drug use.

The technology provides methods of producing normorphine using a reductive agent. In the exemplary embodiments herein provided, the reductive agent is L-selectride. Of course, L-selectride is not the exclusive reductive agent and others may be used, in accordance with the present inventive technology. L-selectride is preferred herein because it is conveniently obtained in a solution with tetrahydrofuran.

Figure 1:
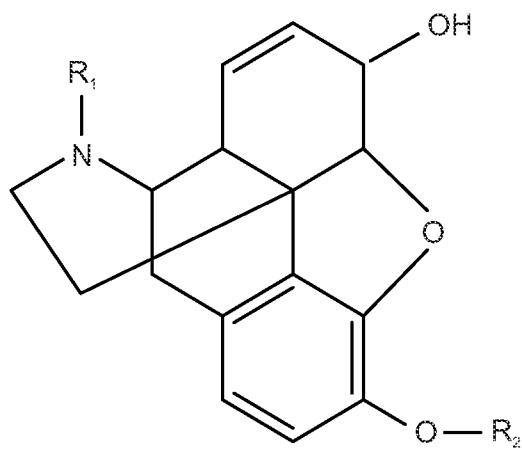
FIG. 1 depicts the molecular structure of morphine (I), a bis-carbonate (II) and normorphine (III) based on the respective identities of $R_1$ and $R_2$, shown in the Key.

FIG. 1 illustrates a structural formulae for variants of morphine (I), a bis-carbonate (II) and normorphine (III) based on the respective identities of $R_1$ and $R_2$, shown in the Key. Of course, other moieties may also be substituted for $R_1$ and $R_2$.

Figure 2:
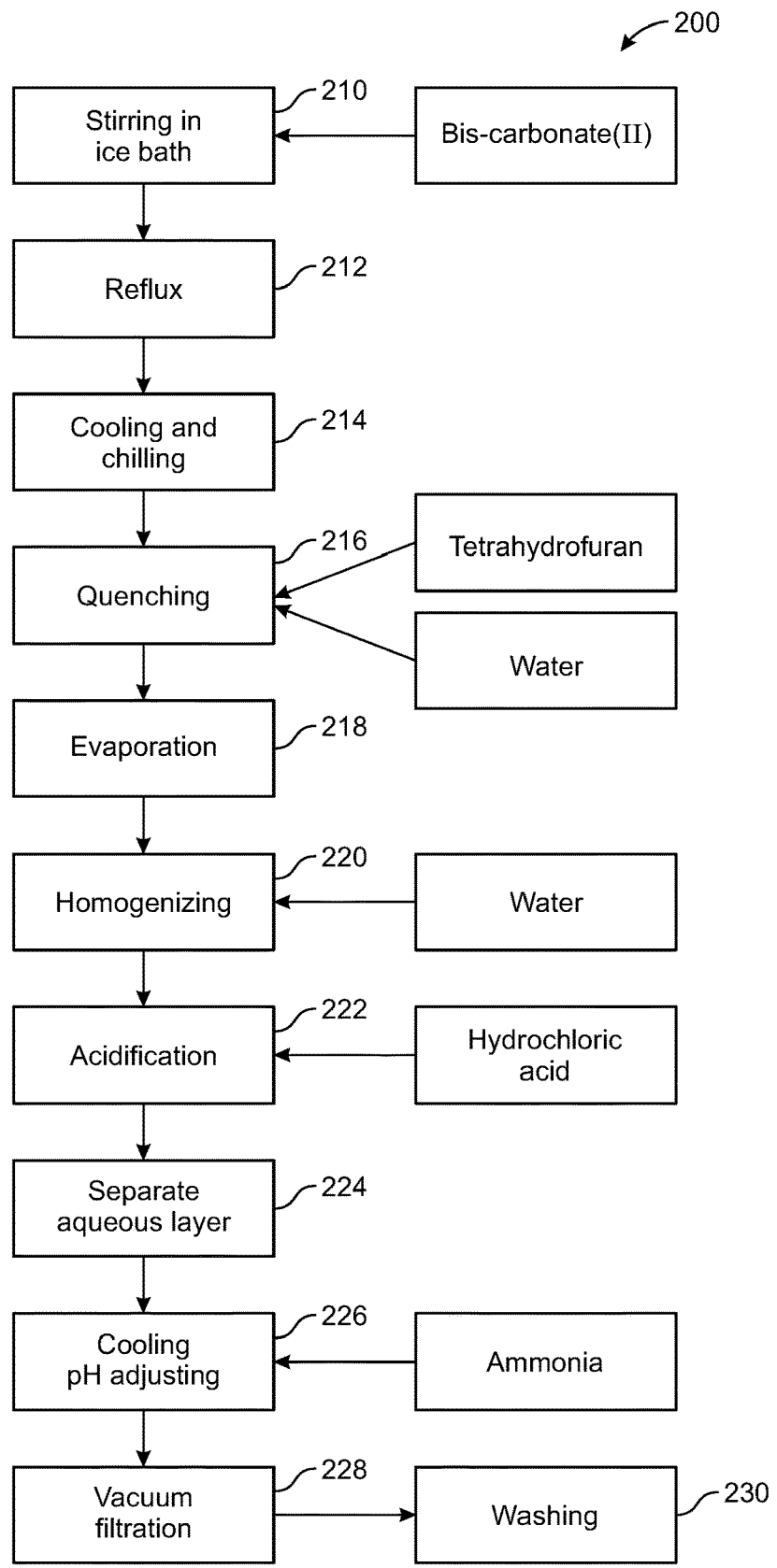
FIG. 2 is a flow chart illustrating steps in an exemplary embodiment of the process of making normorphine by reacting a morphine bis-carbonate with a reductive agent.

The process flowchart of FIG. 2 illustrates an exemplary method 200 of making normorphine using a reductive agent. The process may be amended or simplified, of course based on the teachings provided herein. In step 210 a solution of L-selectride in a solution with tetrahydrofuran is stirred in an ice bath at about 0-5° C. As pointed out above, reductive agents other than L-selectride may also be useful. Moreover, whereas in the described embodiment the solvent is tetrahydrofuran, other solvents such as dioxane, or similar ethers may also be useful. L-selectride in solution with tetrahydrofuran is readily available. To this mixture, bis-carbonate (II)

in a tetrahydrofuran solution is added dropwise over a period of about 10-15 minutes. After addition, in step 212, the mixture is refluxed for about 20-50 hours. In step 214, the mixture is cooled, for example in a water bath, then chilled to about 0-5° C. In step 214 the chilled mixture is quenched to of any remaining reactive material by adding dropwise tetrahydrofuran (diluted with water; tetrahydrofuran:water 10:1 v/v). This is followed by adding water dropwise. In step 218 the solvent (tetrahydrofuran in this embodiment) is removed by evaporation. The residue is collected in step 220 and homogenized in water with stirring. In step 222, the homogenized mixture is acidified with hydrochloric acid to a pH of about 1. As a result, two layers are formed. In step 224 the aqueous layer is separated. In step 226, this layer is cooled in a cold-water bath and treated with a neutralizing agent, in this instance concentrated ammonia may be used, to achieve a pH in the range about 8-9. A white crystalline deposit is formed. The crystalline solid is separated out under vacuum filtration, in step 228. The solid may be washed with water and dried to obtain a reaction product that contains normorphine, typically at about 75 to 78 wt % yield.

Figure 3:
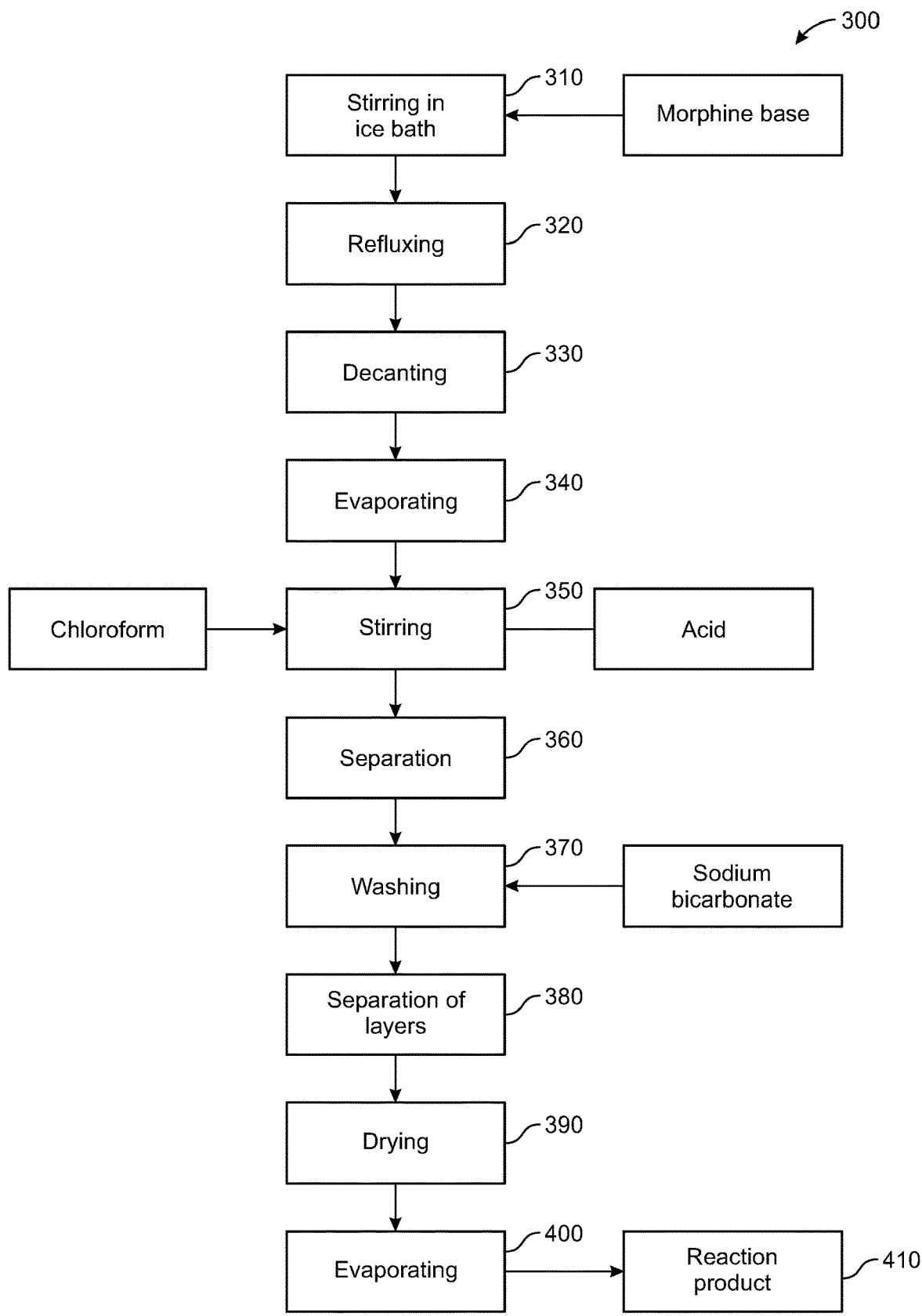
FIG. 3 is a flow chart illustrating steps in an exemplary embodiment of the process of making a bis-carbonate that may be used in the production of normorphine.

In the foregoing, the description assumes the availability of morphine bis-carbonate. In FIG. 3, there is presented an illustrative flowchart providing the steps in making morphine bis-carbonate. In step 310 morphine base is added to a stirred mixture of a chloroformate, for example including, but not limited to, methyl chloroformate, ethyl chloroformate, a lower alkyl chloroformate or a benzoic type-chloroformate; and to a bicarbonate, such as sodium bicarbonate, in chloroform. The stirring continues for about 15 minutes, then the mixture is brought to reflux, in step 320 for about 20 to 50 hours. After cooling to room temperature (about 18 to 22° C.), the mixture is decanted in step 330 and a solid residue is obtained. In step 340, the residue is evaporated under vacuum. The residue is then stirred with chloroform and hydrochloric acid at a pH of about 1 for about 2 hours, in step 350. The mixture is then separated, in step 360, and a chloroform extract is obtained and washed with saturated sodium bicarbonate, in step 370. The chloroform layer is then separated in step 380, and dried in step 390, over magnesium sulfate or the like. The dried product is evaporated in step 400 to produce a syrup in step 410 which contains a bis-carbonate suitable for use in making normorphine as discussed here above.

EXAMPLE

This example illustrates the production of normorphine (III) from morphine using L-selectride as a reductive agent. Of course, the example is non-limiting and is provided for illustrative purposes only.

Step 1: Producing Morphine N,O COOCH$_3$ (II) (Aka "Bis-Carbonate (II)" Herein):

To a stirred mixture (118 ml) of methyl chloroformate (146 g) (1.5 moles), 115 g sodium bicarbonate (1.37 moles) and 1.3 L of chloroform was added 26.2 g (0.092 moles) of morphine base. The mixture was stirred at room temperature (about 20° C.) for 15 minutes then slowly warmed to reflux. The mixture was refluxed while stirring for 45 hours and cooled to room temperature. Then the (liquid) mixture was decanted from the solids and evaporated under vacuum to provide a residue.

The residue was stirred with 100 ml of chloroform and 150 ml of 1N hydrochloric acid for 2 hours. The mixture was separated, and the chloroform extract obtained was washed with 100 ml saturated sodium bicarbonate. The chloroform layer was separated, dried over magnesium sulfate and then evaporated to produce 34.5 g of a syrup. An infrared spectrum of the syrup showed clear, strong signals for the 3-O—COOCH$_3$ ester at 1756 cm and at 1693 cm for the N-carbamate.

Step 2: Producing Normorphine (III)

To a solution of 225 ml of L-Selectride (1M in tetrahydrofuran) at a temperature in the range 0-5° C. (in an ice bath) was added dropwise over 10 minutes a solution of bis-carbonate (II), being 12.0 g in 20 ml of tetrahydrofuran. The cooling bath was removed, and the solution was brought to reflux which was maintained for 45 hours.

The refluxed mixture was then cooled to room temperature before being chilled in an ice bath to 0-5° C. To quench any remaining reagent, a solution of 10 ml tetrahydrofuran diluted with 1 ml of water was added carefully dropwise. This was followed by careful addition of 3 ml water dropwise to ensure complete decomposition of any reactive material. Thereafter, tetrahydrofuran was removed by evaporation to produce a residue.

The residue was cooled in a cold-water bath and treated with addition of 100 ml water followed by stirring to achieve homogeneity. The stirred mixture was then acidified by adding dropwise 25 ml concentrated hydrochloric acid (12 M) to achieve a pH of about 1.

The layers formed in the acidified mixture were separated. The lower aqueous layer was cooled in a cold-water bath and treated with concentrated ammonia until a pH of 8-9 was achieved. A white crystalline precipitate formed, and after chilling for 2 hours, it was collected by vacuum filtration. The water-washed cake was dried to produce 6.75 g (78 wt. %) of normorphine (III). An infrared spectrum showed complete removal of the 1756 and 1693 cm' bands.

The foregoing specification enables the production of normorphine (III), using a reductive agent, by suitable selection of reactants and process steps.

The foregoing, which sets forth aspects of the inventive methods of facile conversion of morphine to normorphine, does not limit the scope of the inventive technology which is defined by the scope of the appended claims, as properly construed by a court of competent jurisdiction.

What is claimed is:

1. A method of making normorphine, the method comprising the steps of:
   preparing a solution of a morphine bis-carbonate in a solvent;
   combining the bis-carbonate solution with a reductive agent in a solvent as a mixture;
   refluxing the mixture;
   quenching any remaining reagent in the refluxed mixture;
   evaporating solvent to produce a residue;
   homogenizing the residue with water;
   acidifying the homogenized residue;
   neutralizing the acidified homogenized residue;
   separating and removing an aqueous layer from the neutralized homogenized residue;
   cooling the aqueous layer and adjusting to a pH in the range about 8 to about 9 to produce a crystalline precipitate; and
   filtering to collect a reaction product comprising normorphine.

2. The method of claim 1, wherein the step of preparing in a solvent comprises tetrahydrofuran as the solvent; and wherein the step of combining comprises using L selectride as the reductive agent.

3. The method of claim 1, wherein the step of combining comprises combining with L-selectride in a tetrahydrofuran solution, dropwise, in an ice-bath at about 0-5° C.

4. The method of claim 1, wherein the step of refluxing continues for about 20 to 50 hours.

5. The method of claim 1 wherein the step of acidifying comprises using concentrated hydrochloric acid as an acidifying agent.

6. The method of claim 1 wherein the step of cooling to produce a precipitate includes chilling for about 2 hours.

7. The method of claim 1, wherein the step of quenching comprises adding a mixture of a solvent containing water.

8. The method of claim 1, wherein the step of quenching includes adding water as a quench.

9. The method of claim 1, further comprising, after the step of filtering to collect, a step of washing the reaction product with water.

10. The method of claim 1, further comprising making the morphine bis-carbonate used in the step of preparing a solution of bis-carbonate, wherein making the morphine bis-carbonate used in the step of preparing a solution of bis-carbonate further comprises:

adding morphine base to a mixture of methyl chloroformate and sodium bicarbonate in chloroform, while stirring;
refluxing the mixture;
decanting from a solid material;
evaporating the solid material;
stirring the evaporated solid material with chloroform and acid;
separating a chloroform extract;
washing the separated extract with sodium bicarbonate;
separating a chloroform layer;
drying and evaporating the chloroform layer; and
obtaining a syrup product comprising bis-carbonate.

11. The method of claim 10, wherein the step of refluxing includes refluxing for about 20 to 50 hours.

12. The method of claim 10, wherein the step of stirring comprises stirring while adding chloroform and hydrochloric acid.

13. The method of claim 10, wherein the step of washing comprises washing with a sodium bicarbonate solution.

14. The method of claim 10, wherein the step of drying comprises drying over magnesium sulfate.

\* \* \* \* \*